United States Patent [19]

Silver et al.

[11] 4,097,602

[45] Jun. 27, 1978

[54] METHOD OF INHIBITING BLOOD PLATELET AGGREGATION

[76] Inventors: Melvin J. Silver, 6640 Wissahickon Ave., Philadelphia, Pa. 19119; John Bryan Smith, 40 Needlepoint Lane, both of Philadelphia, Pa. 08016; Carol M. Ingerman, 40 Needlepoint La., Willingboro, N.J.

[21] Appl. No.: 717,277

[22] Filed: Aug. 24, 1976

Related U.S. Application Data

[63] Continuation of Ser. No. 528,594, Nov. 29, 1974, abandoned.

[51] Int. Cl.$^2$ .................. A61K 31/19; A61K 31/20; A61K 31/215
[52] U.S. Cl. .................................. 424/305; 195/1.7; 424/317; 424/318
[58] Field of Search .................. 424/305, 317, 318; 195/1.7, 1.8

[56] References Cited

FOREIGN PATENT DOCUMENTS 1,082,624  9/1967  United Kingdom ................. 424/318

OTHER PUBLICATIONS

Silver, Prostaglandins, vol. 4, Dec. 1973, pp. 863–875.
Silver, Prostaglandins, vol. 1, Jun., 1972, pp. 429–436.
Shio, Prostaglandins, vol. 1, Jan. 1972, pp. 29–36.
Downing, Prostaglandins, vol. 1, Jun. 1972, pp. 437–441.
Willis, Prostaglandins, vol. 4, Jul. 1973, pp. 127–130.
Bergstrom, Science, vol. 157, Jul. 28, 1967, pp. 382–391.
Pace-Asciak, Biochim. Biophys. Acta, vol. 152, 1968, pp. 787–790.
Ahern, Biochem. Biophys. Acta, vol. 210, 1970, pp. 456–461.
Warner, Chem. Abs., vol. 70, 1969, Ab. No. 18322m.
Zellerhoff, Chem. Abs. vol. 73, 1970, Ab. No. 38573j.
Leonardi, Fed. Proc., vol. 31, 1972, Ab. No. 202.
Willis, Science, vol. 183, Jan. 25, 1974, pp. 325–330.

*Primary Examiner*—Albert T. Meyers
*Assistant Examiner*—A. P. Fagelson
*Attorney, Agent, or Firm*—Benasutti Associates, Ltd.

[57] ABSTRACT

A method for inhibiting blood platelet aggregation by the oral or parenteral administration to a mammal of all cis-8,11,14-eicosatrienoic acid, a compound having the formula:

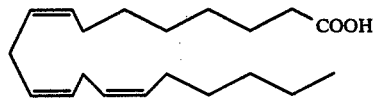

Also disclosed are other fatty acids exhibiting blood platelet aggregation inhibition properties.

15 Claims, No Drawings

METHOD OF INHIBITING BLOOD PLATELET AGGREGATION

This is a continuation of application Ser. No. 528,594, filed Nov. 29, 1974, now abandoned.

BACKGROUND OF THE INVENTION

The present invention relates to a novel and useful method for inhibiting blood platelet aggregation.

Blood platelets, sometimes referred to as thrombocytes, are anucleate cells which exist in large numbers in normal mammalian blood and form a vital part of the complex hemostatic mechanism. When blood vessels are injured and bleeding occurs, blood platelets adhere to subendothelial tissue in the damaged vessel wall and then clump or aggregate to form a platelet plug which arrests the bleeding. This platelet plug is then consolidated by the formation of a network of fibrin which results from activation of the blood clotting system. The pathological extension of the normal hemostatic platelet plug is called a thrombus. This may occur in vessels where the inner wall is injured and bleeding does not occur as, e.g., in atherosclerosis. During thrombus formation, emboli (consisting of platelet aggregates or particles of the more developed thrombus) may go downstream in the blood, lodge in small vessels to completely occlude them and block the flow of blood to a major organ. Thrombosis appears to play an important role as an etiologic or complicating factor in a large number of disease states. While controversy continues as to the causal role of blood-platelet aggregation in atherosclerosis, it is accepted that such platelet aggregation accelerates the narrowing and eventual closure of the vascular lumen begun by the atherosclerotic plaque.

A factor which may be involved in these pathological (thrombocytopathic) phenomena is abnormal blood platelet adhesiveness or stickiness. Regardless of the mechanism, it is generally conceded that thrombosis plays a critical role in stroke, pulmonary embolism and in myocardial infarction. It is generally believed that if this tendency toward undesired platelet aggregation or adhesiveness could be reduced, the incidence of thrombotic episodes would be reduced.

Certain prostaglandins, particularly those of the "E" series, such as 11$\alpha$,15(S)-dihydroxy-9-oxy-13-trans-prostenoic acid (PGE$_1$). 11$\alpha$,15(S)-dihydroxy-9-oxy-13-trans,8-isoprostenoic acid (8-iso PGE$_1$) and, 11$\alpha$,15(S)-dehydroxy-9-oxo-13-trans-homo-prostenoic acid (-homo-PGE$_1$). have been demonstrated to inhibit platelet aggregation, Biochem. Biophys. Acta. vol. 187, pages 285 to 292, 1969, and Circulation, vol. 38, Supp. 4, VI-23, 1968. However, while the above disclosed prostaglandins are known to possess platelet anti-aggregating properties, their use for preventing thrombosis has been seriously limited because their anti-aggregating properties are rapidly destroyed in the circulation during passage through the lungs by an enzyme (PG dehydrogenase) which converts the 15-OH function to a ketone. The administration of these prostaglandins is also associated with several undesirable side effects. Additionally, the prostaglandins of the "E" series readily undergo auto-oxidation to other forms of prostaglandins that lack platelet anti-aggregation properties: Methods of Biochemical Analysis, vol. 17, pages 325 to 371, 1969. Thus, in view of this presentation, it becomes immediately apparent that a critical need exists for a method for inhibiting aggregation of platelets that is essentially free from the tribulations associated with the prior art. Likewise, it will be further apparent that if a new and useful method for protecting platelets is made available to the art, especially wherein the platelet anti-aggregation agent possesses stability, said method would have a positive medical value and it would also present a substantial contribution to the art.

Smith et al. in the British Journal of Pharmacology 40, 545 P (1970), demonstrated that human blood platelets can form and release prostaglandins PGE$_2$ and PGF$_{2\alpha}$ when the washed platelets are treated with thrombin. Silver et al. in Prostaglandins 1, pp. 429–436 (1972), showed that these prostaglandins were formed during blood clotting. They are also formed during the aggregation of platelets in platelet-rich plasma in response to collagen, epinephrine, adenosinediphosphate (ADP), Smith et al., J. Clin. Invest. 52, pp. 965–969 (1973). The precursor of these prostaglandins is arachidonic acid (5,8,11,14-eicosatetraenoic acid). It has been shown that arachidonic acid induces both platelet aggregation and prostaglandin synthesis. During the bioconversion of arachidonic acid to PGE$_2$, PGF$_{2\alpha}$, and other polar products which occur in platelets, such as the 15-OH, 9,11-endoperoxide (variously termed LASS, PGR$_2$ or PGH$_2$) transiently accumulate. LASS induces platelet aggregation. LASS can also induce the release of aggregatory substances from stores within the platelet. The biological effects of LASS are potentiated (up to ~700%) in the presence of submicrogram concentrations of PGE$_2$, Silver et al. Prostaglandins 4 863 (1973). Arachidonic acid esters are present in phospholipids, cholesterol esters, and triglycerides of blood and other tissues and non-esterified arachidonic acid is bound to plasma albumin. Arachidonic acid levels in the body should be affected by consumption of meats and other food items containing this material. Arachidonic acid may function as a hemostatic agent by inducing platelet aggregation if used in the proper amounts, when needed. Inability to release sufficient arachidonic acid or prevention of platelets from participating in PG synthesis, could result in a bleeding tendency. On the other hand, the sudden availability of larger amounts of arachidonic acid could cause thrombosis.

It is therefore an object of this invention to provide a method of inhibiting or preventing blood platelet aggregation by the use of certain fatty acids, particularly 8,11,14-eicosatrienoic acid (dihomo-$\gamma$-linolenic acid.)

SUMMARY OF THE INVENTION

The instant invention relates to a method of inhibiting blood platelet aggregation by the administration, either orally or parenterally, to a patient disposed toward undesirable platelet aggregation, of certain unsaturated fatty acids, particularly 8,11,14-eicosatrienoic acid, or pharmaceutically acceptable salts and esters thereof.

8,11,14-eicosatrienoic acid is generally obtained by pressing vegetable oils, e.g., cottonseed, soybean, sunflower, etc. to obtain $\gamma$-linolenic acid which is bound in complex esters. This material is then hydrolyzed, purified to yield the free $\gamma$-linolenic acid. The free $\gamma$-linolenic acid is then chain extended by standard organic synthetic methods to yield 8,11,14-eicosatrienoic acid.

Although there are materials known to have blood platelet anti-aggregation properties, e.g., aspirin, indomethacin, adenosine and sodium salicylate, they normally possess some disadvantages, i.e., limited effectiveness, long term toxic effects. A distinct advantage of using 8,11,14-eicosatrienoic acid which is present naturally in small amounts in mammalian tissues, to inhibit platelet aggregation is the fact that it is biologically incorporated into the body, therefore not requiring total adherence to a daily dosage schedule.

This invention provides an effective means of inhibiting blood platelet aggregation without the side-effects and disadvantages of platelet inhibitors known heretofore.

DETAILED DESCRIPTION OF THE INVENTION

As used herein, the term "platelet rich plasma" (PRP) refers to the supernatant plasma obtained after slow centrifugation of mammalian blood. It contains large numbers of blood platelets but few red or white cells.

Also used herein, the term "aggregating agent" refers to an agent which induces blood platelet aggregation.

As used herein, the term "potentiator" refers to an agent which acts to enhance aggregation caused by mild aggregation stimulators but will not itself induce platelet aggregation in the concentrations employed.

As used herein, the term "non-aggregating substance" refers to a substance which neither inhibits nor induces blood platelet aggregation.

As used herein, the term "inhibitor" refers to an agent which inhibits blood platelet aggregation.

As used herein, the term "lower alkyl" refers to both straight and branched chain hydrocarbon groups containing from one to six carbon atoms such as methyl, ethyl, propyl, isopropyl, etc.

As used herein, the term "labile aggregation stimulating substance" (LASS), refers to a particular agent which induces platelet aggregation.

As still further used throughout this application, in the pictorial representations of the compounds of this application, a thickened tapered line ◄ indicates a substituent which is in the $\beta$-orientation (above the plane of the molecule), a dotted line ( - - - ) indicates a substituent which is in the $\alpha$-orientation (below the plane of the molecule) and a wavy line ∿∿ indicates a substitutent which is in either the $\alpha$- or $\beta$-orientation. It is to be understood that the pictorial representations of the compounds given throughout the specification are set forth for convenience and are to be construed as inclusive of other forms, including enantiomers and racemates, and are not to be construed as limited to the particular form shown.

As stated previously, human blood platelets form and release prostaglandins $PGE_2$ and $PGF_{2\alpha}$, the precursor of which is arachidonic acid. Arachidonic acid is known to induce both prostaglandin synthesis and blood platelet aggregation.

It has now surprisingly been found that the biosynthesis of $PGE_1$ and $PGF_{1\alpha}$ from 8,11,14-eicosatrienoic acid proceeds through an intermediate PGH or $PGR_1$, which has no effect on blood platelet aggregation. $PGE_1$ is a very potent inhibitor of platelet aggregation. In contradistinction thereto, the bioconversion of arachidonic acid to $PGE_2$ and $PGF_{2\alpha}$ proceeds through an intermediate (variously called LASS or $PGR_2$), which induces blood platelet aggregation. This is quite surprising because arachidonic acid and 8,11,14-eicosatrienoic acid differ by only the presence of an additional double bond in the former compound.

The biosynthesis procedure and contrasting results are illustrated below:

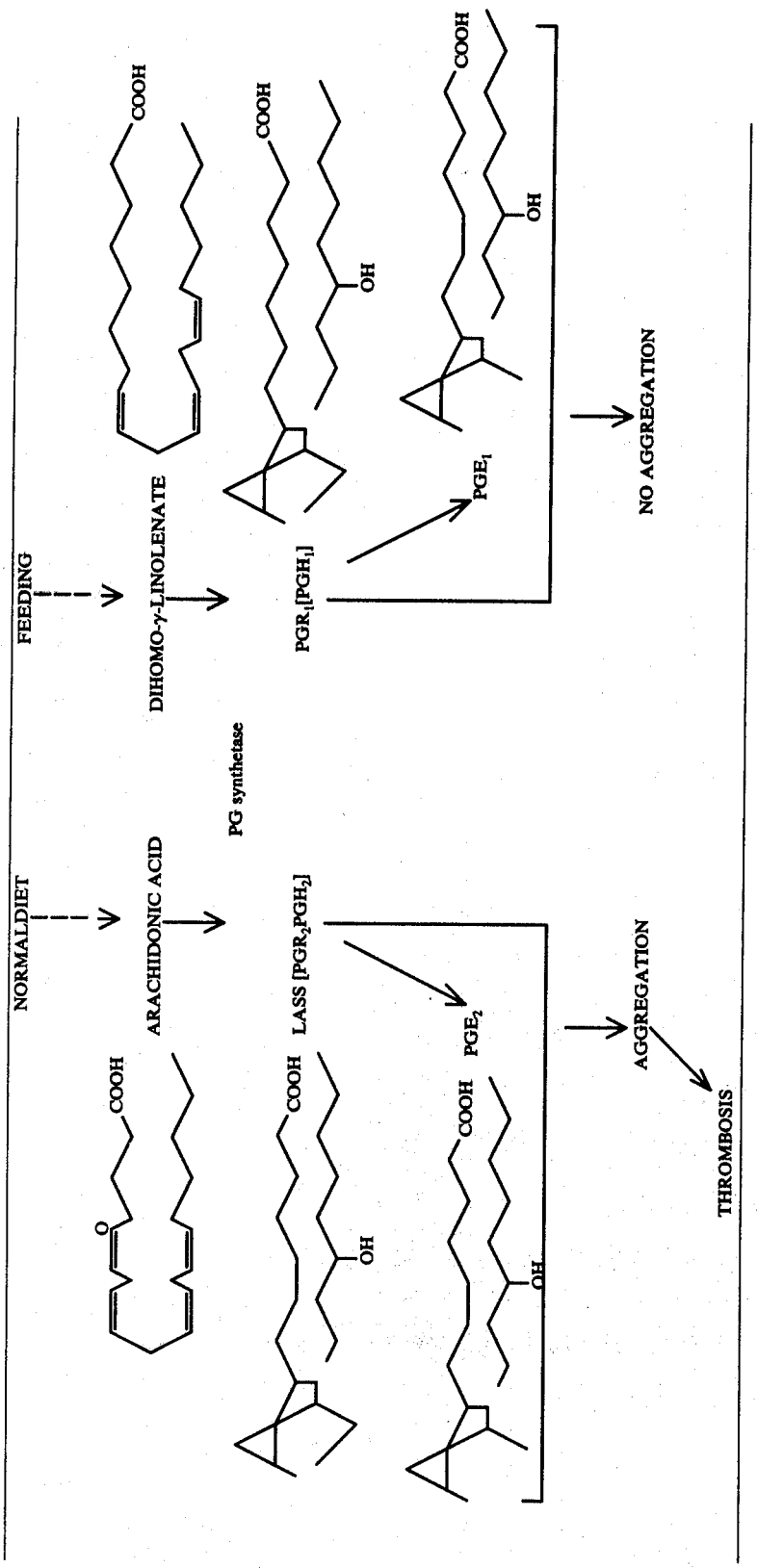

While not wishing to be bound by any particular theory, it is believed that the above sequence is an outline of the mechanism through which orally ingested 8,11,14-eicosatrienoic acid inhibits platelet aggregation and hence arterial thrombosis. Normally, very little 8,11,14-eicosatrienoic acid is found in platelets or the surrounding plasma, but arachidonic acid is readily available. During the platelet prostaglandin synthesis induced by collagen and most other stimuli, the 15-OH endoperoxide intermediate (LASS, PGR$_2$, PGH$_2$) transiently accumulates and induces irreversible aggregation and the platelet release reaction. This effect is dramatically potentiated by PGE$_2$. In vivo, this aggregation could produce a platelet thrombus leading to stroke, myocardial infarction or pulmonary embolism.

Although arachidonic acid will cause platelet aggregation at levels of about 0.1 to 1 micromole per ml. of platelet-rich plasma, it has also been found that lower levels of arachidonic acid, e.g., less than 0.1 $\mu$mole/ml. will enhance aggregation caused by collagen, ADP, or epinephrine. In short, arachidonic acid is both a potentiator and an aggregating agent. Arachidonic acid causes platelet aggregation and a lethal pulmonary embolism when injected into the ear veins of rabbits at a dose of 1.4 mg/kg body weight, Silver et al. 183, 1085–1087 (1974). That arachidonic acid may have similar effects is suggested in human by the finding that platelet aggregates were found in the lungs of humans after unexplained sudden death. Pirkle et al., Science 185, 1062–1064 (1974).

That LASS may be the causative factor in arterial thrombosis is based on the fact that aspirin, which has anti-thrombotic properties in laboratory animal models of arterial thrombosis, inhibits the biosynthesis of LASS.

Oral feeding with 8,11,14-eicosatrienoic acid leads to its accumulation, so that it can complete with arachidonic acid for platelet PG synthetase. The endoperoxide (PRG$_1$, PGH$_1$) formed does not induce platelet aggregation. In addition, the PGE$_1$ end-product produced can potently inhibit aggregation.

It has been found that 8,11,14-eicosatrienoic acid inhibits platelet aggregation at concentrations between 0.05 $\mu$M/ml to about 0.5 $\mu$M/ml of platelet-rich plasma (in vitro). An effective dosage for inhibiting blood platelet aggregation in vivo may be from about 5 to about 400 mg/kg per day, preferably 100 mg/kg.

Although the emphasis thus far has been placed on 8,11,14-eicosatrienoic acids, it is to be understood that the use of fatty acids such as 11,14,17-eicosatrienoic acid; 5,8,11,14,17-eicosapentaenoic acid; 5,8,11,14-eicosatetraynoic acid; 4,7,10,13,16,19-docosahexaenoic acid; are also within the scope of this invention.

The composition of this invention can be administered to mammals disposed toward undesirable (excessive) blood platelet aggregation. Individuals can be disposed to hyperthrombotic complications due to surgery, late pregnancy, phlebitis, atherosclerosis, recent myocardial infarction, and the like. The compositions of the invention are particularly suited for administration to patients who have just had artificial heart valves inserted and therefore face a serious risk of thromboembolism from platelet thrombi. It is also contemplated that the process of this invention can be employed as long term prophylactic treatment of persons disposed to excessive platelet aggregation. The compositions of this invention can be administered either orally or parenterally. The oral route is preferred for chronic and prophylactic use. Parenteral use is indicated for those excessively prone to acute thromboembolic episodes, and when immediate onset of activity is desired. In each specific instance, the attending diagnostician will determine the exact dosage, amount and frequency taking into account related health factors of the subject.

For oral use, the fatty acids employed herein can be combined with conventional compatible organic or inorganic pharmaceutical carrier materials known in the art. Such materials include, for example, water, gelatin, gums, lactose, starches, magnesium stearate, talc, vegetable oils, polyalkylene glycols, petroleum jelly and the like. Such pharmaceutical preparations may be in unit dosage form and may additionally contain other therapeutically valuable substances or conventional pharmaceutical adjuvants such as preservatives, stabilizing agents, wetting agents, emulsifying agents, buffers and the like. The pharmaceutical preparations can be in conventional solid dosage forms such as tablets, capsules, dragees and the like, conventional liquid forms such as solutions, suspensions, emulsions and the like and other conventional dosage forms such as dry ampules, suppositories and the like. Such preparations may be submitted to conventional pharmaceutical expedients such as, for example, sterilization and the like.

For parenteral use, fatty acids employed herein can be administered in conventional pharmaceutical forms, preferably parenteral forms, for example, solutions, suspensions and emulsions. Examples of conventional pharmaceutical carrier materials which may be utilized in such forms include, for example, water for injection, vegetable oils, polyalkylene glycols and the like. Such preparations can be subjected to conventional pharmaceutical expedients such as sterilization and can contain conventional pharmaceutical adjuvants such as preservatives, stabilizing agents, wetting agents, emulsifying agents, salts for the adjustments of osmotic pressure, buffers and the like. The composition can also contain other therapeutically active materials.

The following non-limiting examples illustrate the instant invention. In the examples, arachidonic acid is designated as 20:4$\omega$6 and the 8,11,14-eicosatrienoic acid as 20:3$\omega$6.

Determination of Prostaglandins. PGE$_2$ and PGE$_1$ were measured by bioassay after extraction from plasma and separation of PGE and PGF fractions on columns of silicic acid. Further separation of prostaglandins was obtained by thin layer chromatography. PGF$_{2\alpha}$ was determined by radioimmunoassay using the nitro-cellulose filter method* and a PGF$_{2\alpha}$ anti-serum.

*Levine, L., Gutierrez-Cernosek, R.M., Polet, H. and Gershman, H. Prostaglandins: Serologic Specifications and Estimation in Biological Fluids, in Prostaglandins in Fertility Control, Bergstrom, S., Green, K., Samuelsson, B., Eds., WHO Conference, Stockholm, 1972, p. 38.

Other reagents used in these studies included collagen, adenosine, epinephrine-HCl and ADP.

Example 1

In order to measure the blood platelet aggregation response to various aggregating agents, the following procedure was employed.

Blood, human and animal, was collected in 0.1 volume of 3.8% trisodium citrate and centrifuged at 250 g for 15 minutes at 20°–22° C. to prepare an upper layer of platelet-rich plasma (PRP). Aggregation of the platelets was studied photometrically in siliconized tubes at 37° C. with the continuous recording of light transmission (Aggregometer, Chronolog Corp., Broomall, Pa.).

Each experiment was conducted by comparing the light transmission of a control (PRP in saline) with the light transmission of a sample of PRP containing aggregation agent or inhibitor. Aggregation was allowed to go on for about 3 minutes. The "initial rate of aggregation" refers to the maximal rate of increase of light transmission occurring within 30 seconds addition of an aggregating agent and the "extent of aggregation" refers to the maximal increase of light transmission found after addition of this agent.

The aggregating response of human blood platelets in platelet-rich plasma (PRP) is illustrated below. The sodium salt of arachidonic acid was employed.

| Sodium Arachidonate (Amount) | PRP (Amount) | Initial Rate of Aggregation | Extent of Aggregation |
|---|---|---|---|
| 750 nmoles* | 1.5 ml. | 30 | 65 |

Example 2

In accordance with the procedure of Example 1, the following example illustrates the potentiating effect of arachidonic acid (AA) on human blood platelet aggregation induced by collagen and ADP. As in Example 1, the sodium salt of arachidonic acid was used.

| Aggregating Agent (Amount) | PRP (Amount) | Initial Rate of Aggregation | Extent of Aggregation |
|---|---|---|---|
| Collagen (5 μl) | 1.5 ml. | 3 | 10 |
| Collagen (5 μl) + AA (150 nmoles)* | 1.5 ml. | 8 | 55 |
| ADP 1.5 nmoles* | 1.5 ml. | 15 | 23 |
| ADP 1.5 nmoles* (150 nmoles) | 1.5 ml. | 15 | 52 |

*nmole = nanomole = $10^{-9}$ mole

Example 3

The following example illustrates the relationship between preincubation time of 8,11,14-eicosatrienoic acid with human platelet rich plasma (PRP) and the inhibition of blood platelet aggregation by amount of $PGE_1$ formed.

PRP (16 ml. amounts) was incubated with 8 μmoles of 8,11,14-eicosatrienoic acid (Na salt) for varying periods of time and then 5 ml. amounts were extracted for prostaglandins using chloroform/ethanol at acid pH. The prostaglandin E zone from silicic acid column chromatography was subjected to bioassay on the rat fundus strip and the following results were obtained:

Table 1

| Temp. of Incubation | Time of Incubation (min.) | Prostaglandin $E_1$ formed (pmole/ml PRP)* |
|---|---|---|
| 22° C. | 15 | 24 |
| 22° C. | 45 | 288 |
| 22° C. | 75 | 221 |
| 37° C. | 15 | 94 |
| 37° C. | 45 | 979 |
| 37° C. | 75 | 474 |

*pmole = picomole = $10^{-12}$ mole

The remaining prostaglandin $E_1$-like material from several columns was pooled and subjected to thin layer chromatography on silver impregnated plates. The prostaglandin $E_1$-zone was tested for its effects on platelet aggregation and showed strong inhibition as follows:

| Inhibitor | PRP Amount | Aggregating Agent Tested | Amount | Rate of Aggn. | Extent of Aggn. |
|---|---|---|---|---|---|
| — | 1.5 ml. | ADP (control) | 3 nmoles | 19 | 28 |
| $PGE_1$* | 1.5 ml. | ADP | 3 nmoles | 12 | 9 |
| — | 1.5 ml. | Collagen (control) | 15 μl | 7 | 48 |
| $PGE_1$* | 1.5 ml. | Collagen | 15 μl | 0 | 0 |

*$PGE_1$ was material from TLC zone equivalent to 75 pmole by bioassay.

Example 4

This example illustrates the extent of blood platelet aggregation with and without the fatty acid inhibitors of the instant invention.

In tests for inhibition, the unsaturated fatty acid was either suspended in platelet poor plasma (PPP) or dissolved as the sodium salt and preincubated at 37° (for the times indicated in the table) with the platelet-rich plasma before the addition of an aggregating agent.

Aggregation of the platelets (about 4 × $10^8$ platelets/ml. plasma) was studied photometrically in accordance with Example 1). Aggregation was induced by ADP, a collagen suspension, arachidonic acid as a solution of the sodium salt prepared as described by Silver et al., Prostaglandins 4, 863.

The data is summarized in Table 2.

TABLE 2

| Exp. No. | Inhibitor tested | Pre-Incubation Time Mins. | Final Conc'n.* of Inhibitor | Aggregating Agent | Final** Conc'n. of Agg. Agent | Initial Rate of Aggregation | Extent of Aggregation |
|---|---|---|---|---|---|---|---|
| 1 | 8,11,14 Eicosatrienoic Acid (Na salt) | 1 | — | Arachidonic Acid (Na salt) | 0.25mM | 19,15,15 | 50,51,52 |
|   |   |   | 0.5 mM | " | " | 0,0,0 | 0,0,0 |
| 2 | 8,11,14 Eicosatrienoic Acid (Suspended in PPP) | 1 | — | ADP | 1 μM | 16 | 46 |
|   |   |   | 0.18 mM | ADP | 1 μM | 16 | 31 |
|   |   |   | — | Collagen | 10 μl | 9 | 47 |
|   |   |   | 0.18 mM | Collagen | 10 μl | 1 | 5 |
| 3a | 8,11,14 Eicosatrienoic Acid (Na salt) | 1 | — | Collagen | 30 μl | 15 | 46 |
|   |   |   | 0.5 mM | Collagen | 30 μl | 6 | 19 |
| 3b | 8,11,14 Eicosatrienoic Acid (Suspended in PPP) | 1 | — | Collagen | 30 μl | 7,9 | 25,31 |
|   |   |   | 0.5 mM | Collagen | 30 μl | 3,3 | 11,9 |
| 4 | 8,11,14 Eicosatrienoic Acid (Na salt) | 1 | — | ADP | 2 μM | 31 | 60 |
|   |   |   | 0.15 mM | ADP | 2 μM | 7 | 23 |
| 5 | 8,11,14 Eicosatrienoic Acid (Na salt) | 1 | — | ADP | 2 μM | 29,25,26 | 54,52,54 |
|   |   | 1 | .25 mM | ADP | 2 μM | 27 | 44 |
|   |   | 1 | .5 mM | ADP | 2 μM | 26 | 43 |
|   |   | 3 | .25 mM | ADP | 2 μM | 24 | 40 |
|   |   | 3 | .5 mM | ADP | μM | 24 | 38 |
| 6 | 8,11,14 Eicosatrienoic Acid (Na salt) | 6 | — | ADP | 1 μM | 24 | 27 |
|   |   |   | 1 mM | ADP | 1 μM | 6,16 | 13,18 |

TABLE 2-continued

| Exp. No. | Inhibitor tested | Pre-Incubation Time Mins. | Final Conc'n.* of Inhibitor | Aggregating Agent | Final** Conc'n. of Agg. Agent | Initial Rate of Aggregation | Extent of Aggregation |
|---|---|---|---|---|---|---|---|
| 7 | 8,11,14 Eicosatrienoic Acid (Na salt) | 75 | — | ADP | 1 μM | 18 | 21 |
|   |   |   | 0.5 mM | ADP | 1 μM | 0 | 0 |
| 8 | 11,14,17 Eicosatrienoic Acid (Na salt) | 1 | — | Arachidonic acid | 0.4 mM | 20,20 | 52,46 |
|   |   |   | 0.4 mM | Arachidonic acid | 0.4 mM | 0,0 | 0,0 |
| 9 a | 11,14,17 Eicosatrienoic Acid (Na salt) | 1 | — | Collagen | 30 μl | 15 | 46 |
|   |   |   | 0.5 mM | Collagen | 30 μl | 5 | 15 |
| 9 b | 11,14,17 Eicosatrienoic Acid (Suspended in PPP) | 1 | — | Collagen | 30 μl | 7,9 | 25,31 |
|   |   |   | 0.5 mM | Collagen | 30 μl | 4,5 | 12,17 |
| 10 a | 5,8,11,14,17 Eicosapentaenoic acid (Na salt) | 1 | — | Arachidonic acid | 0.6 mM | 19,17,19 | 54,57,52 |
|   |   |   | 0.25 mM | Arachidonic acid | 0.6 mM | 0 | 0 |
|   |   |   | 0.12 mM | Arachidonic acid | 0.6 mM | 0 | 0 |
| 10 b | 11,14,17 Eicosatrienoic Acid (Na salt) | 1 | 0.06 mM | Arachidonic acid | 0.6 mM | 0 | 0 |
| 11 | 5,8,11,14,17 Eicosapentaenoic acid (Na salt) | 1 | — | Arachidonic acid | 0.4 mM | 12 | 44 |
|   |   | 0.4 mM | Arachidonic acid | 0.4 mM | 1 | 4 |   |
|   |   |   | — | Collagen | 60 μl | 6 | 30 |
|   |   |   | 0.4 mM | Collagen | 60 μl | 5,5 | 23,26 |

*Microliter amounts of 50 mM solutions or suspensions of the inhibitors tested were added to 1.5 ml. amounts of PRP to obtain the final concentration of the inhibitor.
**Microliter amounts of a collagen suspension or concentrated sodium arachidonate or ADP solutions were added to obtain the final concentration of the aggregating agent.

Example 5

Rabbit and guinea pig PRP was prepared by centrifugation of citrated (0.38% trisodium citrate) blood obtained by cardiac puncture. The PRP's were treated with sodium arachidonate (AA) according to the procedure of Example 2. It was observed that sodium arachidonate was even more effective in rabbit or guinea pig PRP than in human PRP. Concentrations between 0.02 and 0.1 mM produced irreversible aggregation in PRP of these species.

To be sure that the decrease in optical density observed in Examples 4 and 5 in response to AA was indeed due to aggregation and not to lysis of platelet membranes, experiments were done to determine the extent of loss of cytoplasmic constituents. It was observed that small amounts of radioactivity were released from platelets prelabelled with $^{14}$C-adenine but large amounts from platelets prelabelled with $^{14}$C-serotonin. These results indicate that AA-induced aggregation involves selective release from the dense granules, but not lysis and loss of cytoplasmic contents.

Example 6

The following example illustrates the effect of 8,11,14-eicosatrienoic acid in vivo in rats.

8,11,14-eicosatrienoic acid was orally administered for 8 days to rats (male wistars of 240 g. starting weight) at a dose of 400 mg/day.** At 4–6 hours on day 8 after the last dose, the blood was withdrawn from the abdominal aorta of the anesthetized animal into heparin (final concentration of 24 units/ml.). Platelet-rich plasma PRP), platelet free plasma (PFP) and platelet "buttons" were prepared by centrifugation. Platelet aggregation was then examined under standarized conditions.* Total lipid extracts of samples of plasma and platelets were analyzed for their fatty acid composition by gas-liquid chromatography.

*Born, G.V.R. Aggregation of Blood Platelets by Adenosine Diphosphate and its Reversal, Nature (London) 194:927, 1962.
**In addition, over the same 8 day period a control group of rats was fed arachidonic acid and similarly another control group was fed neither 8,11,14-eicosatrienoic acid nor arachidonic acid.

In rats treated with 8,11,14-eicosatrienoic acid, the mean plasma 20:3ω6/20:4ω6 ratio rose 16-fold over controls to 0.48 ± 0.11, Table 3 an increase significant at $p < 0.01$. There was in this group, however, a significant increase in the plasma arachidonate levels (56.1%, $p < 0.01$), likely due to bioconversion of the 8,11,14-eicosatrienoic acid. Rats fed arachidonic acid (400 mg/kg) had mean plasma 20:3ω6/20:4ω6 ratios of 0.011 ± 0.002, a value not significantly different from controls. In these animals the plasma arachidonate levels increased 126% ($p < 0.001$) over controls. Similar results were obtained when platelet lipids were extracted and analyzed.

In PRP from the rats which had received 8,11,14-eicosatrienoic acid aggregation responses induced by collagen or ADP were generally reduced, and although there was some variability, aggregation response was virtually abolished in two cases. The mean aggregation response extent induced by collagen at 180 or 450 μg/ml was 31.2 ± 11.1 and 56.7 ± 7.6 respectively, for PRP from rats treated with 8,11,14-eicosatrienoic acid and in which the plasma 20:3ω6/20:4ω6 ratios were > 0.1. A comparison of these values to the means of the combined control (there was no significant differences between untreated and arachidonic acid-treated rats controls) revealed that these aggregation responses to the two levels of collagen were reduced to 55% and 70%, respectively, of the control values. The response to ADP was reduced by 63%. These reductions were significant at p values of 0.025 or less.

These results are tabulated in Table 3.

TABLE 3

| | DIETARY ALTERATION OF RATE PLATELET AGGREGATION | | | |
|---|---|---|---|---|
| Experiment | Controls (5)+ | 20:4ω6 Controls (7)+ | Combined Control (12)+ | 20:3ω6 (6)+ |
| | | (Ave ± S.E.M.) | | |
| Plasma 20:3ω6/20:4ω6 | 0.030 ± 0.009 ($p < .005$)** | 0.011 ± 0.002* ($p < .001$) | 0.019 ± 0.005 ($p < .001$) | 0.48 ± 0.11 |
| Aggregation Extent: | | | | |
| Collagen (180 μg/ml) | 56.4 ± 6.9 ($p < .1$) | 56.8 ± 5.4 ($p < .1$) | 56.6 ± 4.1 ($p < .025$) | 31.2 ± 11.1 |
| Collagen (450 μg/ml) | 82.8 ± 3.5 | 80.3 ± 3.1 | 81.3 ± 2.2 | 56.7 ± 7.6 |

TABLE 3-continued

| | DIETARY ALTERATION OF RATE PLATELET AGGREGATION | | | |
|---|---|---|---|---|
| Experiment | Controls (5)[+] | 20:4ω6 Controls (7)[+] | Combined Control (12)[+] | 20:3ω6 (6)[+] |
| ADP (1 μg/ml) | (p<.025)<br>56.1 ± 5.1<br>(p<.1) | p<.025)<br>58.4 ± 3.9<br>(p<.025) | p<.001)<br>57.4 ± 3.0<br>(p<.01) | 36.1 ± 7.9 |

[+]Indicates number of animals.
*The plasma 20:3ω6/20:4ω6 ratio of the arachidonate fed control rats was not significantly different from the controls at 0.1 > p > 0.05.
**Value in parenthesis indicates the level of significance when results were compared to the results of the 20:3ω6 fed rats.

Example 7

The following example illustrates the effect of 8,11,14-eicosatrienoic acid in rabbits. These results demonstrate an increase in platelet 20:3ω6 when the rabbits are fed 8,11,14-eicosatrienoic acid. Five New Zealand white male rabbits (2 kg. body weight) were orally administered 100 mg/kg of ethyl ester and five untreated rabbits were utilized as control.

There was a marked increase in the plasma and platelet ratio of 20:3ω6/20:4ω6 from control levels of >0.1 up to a value approaching 1.0. For example, mean ratio of 20:3ω6/20:4ω6 in the platelets was 0.030 ± .012 for control animals and 0.88 ± 0.20 for treated animals. This 30-fold increase was significant at p<0.005.

Such increases in 20:3ω6/20:4ω6 were even more striking in platelet-free plasma. Accompanying these increases, there was a corresponding inhibition of aggregation induced by collagen, ADP or chromatographically purified LASS.

Example 8

The following example illustrates the in vitro effects of 8,11,14-eicosatrienoic acid (or salt thereof) on LASS formation. These effects were determined by measuring the extent of platelet aggregation.

A mixture containing equimolar amounts of arachidonic acid and 8,11,14-eicosatrienoic acid was incubated with a PG synthetase preparation obtained from sheep vesicular gland. At the end of the reaction, LASS was purified by liquid chromatography and thin layer chromatography and its activity measured. There was a reduction in LASS activity ranging from about 59.7% to about 76.4%. This indicates that there is competition between the arachidonic acid and 8,11,14-eicosatrienoic acid for the synthetase.

Example 9

The following example illustrates a typical parenteral formulation employing 8,11,14-eicosatrienoic acid suitable for use according to the instant invention.

| Composition: | Per ml. |
|---|---|
| 8,11,14-eicosatrienoic acid | 5.0 mg. |
| Disodium edetate | 0.1 mg. |
| Benzyl alcohol | 0.01 ml. |
| Propyl gallate | 0.05 mg. |
| BHA | 0.05 mg. |
| Sodium bisulfite | 1.0 mg. |
| NaOH (10%)q.s. to pH 9.0-10.0 | |
| Water for injection q.s. to | 1.0 ml. |

We claim:

1. A method for inhibiting blood platelet aggregation comprising administrating to an individual disposed toward undesirable blood platelet aggregation from about 5-400 mg/kg of body weight of 8,11,14-eicosatrienoic acid, the ester thereof or a pharmaceutical acceptable salt thereof.

2. A method according to claim 1 wherein the mode of administration is oral.

3. A method according to claim 1 wherein the mode of administration is parenteral.

4. A method according to claim 1 wherein the amount of said acid administered is 100 mg. per kg. of body weight.

5. A method for inhibiting blood platelet aggregation comprising administering to an individual disposed toward undesirable blood platelet aggregation from about 5-400 mg/kg of body weight of 11,14,17-eicosatrienoic acid, the ester thereof or a pharmaceutical acceptable salt thereof.

6. A method according to claim 5 wherein the mode of administration is oral.

7. A method according to claim 5 wherein the mode of administration is parenteral.

8. A method according to claim 5 wherein the amount of said acid administered is 100 mg. per kg. of body weight.

9. A method for inhibiting blood platelet aggregation by adding to a platelet-rich plasma an effective amount, to essentially inhibit platelet aggregation, of 5,8,11,14,17-eicosapentaenoic acid or pharmaceutically acceptable salts or lower alkyl esters thereof.

10. The method according to claim 9 wherein the concentration range of said acid employed is from about 0.05mM to about 0.5mM per liter of platelet-rich plasma.

11. A method for inhibiting blood platelet aggregation by adding to a platelet-rich plasma an effective amount, to essentially inhibit platelet aggregation, of 11,14,17-eicosatrienoic acid or pharmaceutically acceptable salts or lower alkyl esters thereof.

12. The method according to claim 11 wherein the concentration range of said acid employed is from about 0.05mM to about 0.5mM per liter of platelet-rich plasma.

13. A method for inhibiting blood platelet aggregation by adding to a platelet-rich plasma an effective amount, to essentially inhibit platelet aggregation, of 8,11,14-eicosatrienoic acid or pharmaceutically acceptable salts or lower alkyl esters thereof.

14. A method according to claim 13 wherein the concentration range of said acid employed is from about 0.05mM to about 0.5mM per liter of platelet-rich plasma.

15. A method for inhibiting blood platelet aggregation comprising administering to an individual disposed toward undesirable blood platelet aggregation an effective amount, to essentially inhibit platelet aggregation, of 5,8,11,14,17-eicosapentaenoic acid, a lower alkyl ester thereof or a pharmaceutical acceptable salt thereof.

* * * * *